United States Patent [19]
Vought et al.

[11] Patent Number: 5,251,990
[45] Date of Patent: Oct. 12, 1993

[54] METHOD OF APPLYING SKIN PRODUCTS USING AN ELONGATED STRIP

[76] Inventors: Elizabeth C. Vought; David I. Wood, both of 9141 W. 3rd St., Beverly Hills, Calif. 90210; Albert J. Wood, 300 Orchard Way, Merion, Pa. 19066

[21] Appl. No.: 572,013

[22] Filed: Aug. 24, 1990

Related U.S. Application Data

[63] Continuation-in-part of Ser. No. 400,795, Aug. 30, 1989, abandoned.

[51] Int. Cl.⁵ .............................................. A45D 34/04
[52] U.S. Cl. ......................................... 401/8; 15/222
[58] Field of Search ................... 401/6, 7, 8, 201, 136, 401/137, 139, 261; 15/222; 128/62 R, 67; 604/289, 304, 303, 292

[56] References Cited

U.S. PATENT DOCUMENTS

| | | | |
|---|---|---|---|
| 1,990,568 | 2/1935 | Scheidler | 15/222 |
| 2,233,811 | 3/1941 | Doty | 604/289 |
| 3,061,841 | 11/1962 | Johnson | 401/6 X |
| 3,213,474 | 10/1965 | Toth | 15/222 |
| 3,396,406 | 8/1968 | Gongwer | 128/155 X |
| 3,699,980 | 10/1972 | Carpenter | 401/266 X |
| 3,720,205 | 3/1973 | Liebman | |
| 3,875,933 | 4/1975 | Schwab | |
| 3,973,563 | 8/1976 | Green et al. | 128/156 |
| 4,704,119 | 11/1987 | Shaw et al. | 604/304 X |
| 4,759,652 | 7/1988 | Ulrich | 15/222 X |
| 4,906,118 | 3/1990 | Crooks | 401/8 X |

FOREIGN PATENT DOCUMENTS 727017 5/1932 France ................................... 15/222

Primary Examiner—Danton D. DeMille
Attorney, Agent, or Firm—Hadd S. Lane

[57] ABSTRACT

An applicator is provided for use in placing skin products on a person's body, particularly the recessed areas of the back. The applicator comprises an elongated rectangular strip of flexible material having finger holes at each end. One side of the strip has a non-absorbent, thinner layer of lesser elasticity to which lotion or the like is applied. The other side is a thicker layer of greater elasticity, laminated to the thinner layer. The elasticities are such that when the strip is tensioned, the strip will bulge so that the lotion-receiving layer will contact a recessed area of the body.

2 Claims, 1 Drawing Sheet

METHOD OF APPLYING SKIN PRODUCTS USING AN ELONGATED STRIP This application is a continuation in part of applicator Ser. No. 07/400,795, filed by David Wood and Elizabeth C. Vought, filed Aug. 30, 1989 now abandoned.

BACKGROUND OF THE INVENTION

This invention relates generally to applicators for lotions, creams and similar skin products. More particularly, this invention relates to an applicator device suitable for applying skin products on the inaccessible portions of a user's back.

In the past, people have generally been without an easy and effective way to apply skin products on their backs by themselves. Without another person to assist them, sunbathers have struggled unsuccessfully to put protective lotions and oils on the inaccessible portions of their backs. The application of skin products is extremely necessary for light-skinned people susceptible to skin cancer. Often, the inaccessible portions of their backs are exposed to the harmful rays of the sun without any protective sunscreen due to the difficulty encountered in applying lotion uniformly upon the back. The need for one to be able to apply medication on their back without assistance is especially acute when such medication is necessary to treat contagious skin diseases such as impetigo.

Flexible strips for washing or massaging the inaccessible portions of one's back have been previously provided and generally include handles, or the like, attached at opposite ends of the strip. The handles enable the strip to be grasped and manually rubbed back and forth across one's back. In general, such previous back washers or massagers have not been directed towards effectively applying lotion, or the like, to the back. Previous devices for rubbing one's back are generally inadequate for efficiently applying lotion as well, because the skin-contacting portion of such devices is commonly made of a liquid absorbent material. This creates a problem wherein lotion, or the like, is wasted because it is retained by the liquid absorbent material rather than being transferred to the user's skin.

Previous devices that were directed towards lotion application to the back also suffered from the aforementioned drawback of utilizing a liquid absorbent material which inhibited the transfer of lotion to the body. Other previous applicators required multiple manufacturing steps, such as providing a reinforced pocket for holding lotion, that raised production costs, thereby resulting in an undesirably expensive item. Moreover, previous applicators suitable for back use have not been made available in a disposable, throw-away form, ideal for one-shot usage at a beach, or in hospitals, doctors' offices, etc. Such a disposable applicator would desirably enable a patient to apply medication to the back without the assistance of a nurse.

There exists, therefore, a need for an improved applicator that can easily and efficiently be used to apply skin products or medicine to the back. Such an applicator should utilize a non-absorbent surface that will not retain and waste skin products, and should avoid any mechanical complexities which would increase the manufacturing costs. Additionally, an improved back applicator is needed which can be provided in a disposable, throw-away form for short term usage. Such a disposable applicator should be capable of being configured in a compact form suitable for packaging. Moreover, such an applicator should be capable of being easily and inexpensively manufactured. The present invention fulfills these needs in an inexpensive fashion and provides further related advantages.

SUMMARY OF THE INVENTION

The present invention resides in an improved applicator device for spreading medication or skin products on the body, particularly in the recessed portion of the back. In accordance with the preferred form of the invention, a non-absorbent, mechanically simple applicator is provided which avoids the mentioned drawbacks of prior devices. The applicator generally comprises an elongated, preferably rectangular, strip of flexible material having a thinner layer of non-absorbent material of a desired elasticity on one side, and a thicker layer, or lamination, of material of greater elasticity on the other side, and finger holes at its opposite ends. The holes enable the user to manipulate the applicator in an effective manner.

The use of the non-absorbent surface to apply a desired skin product advantageously prevents the skin product from being wasted by absorption into the applicator. A related advantage is that, because the skin products are transferred onto the skin and not absorbently retained by the applicator, the applicator can be easily and effectively cleaned by wiping with a tissue, or the like, and needs to be washed only occasionally. Because the non-absorbent applicator is easily cleaned and does not retain skin products by absorption, the invention prevents the undesirable situation wherein skin products trapped in an absorbent applicator can spoil and cause skin irritations upon repeated use of the applicator. (This was a common drawback in previous applicators.) The applicator of the present invention advantageously applies fresh skin products each time it is used. When washed, the non-absorbent nature of the applicator enables it to dry quickly for immediate use. A further advantage of the present invention includes the fact that it is not mechanically complex, thereby making the applicator inexpensive to manufacture.

In the preferred form of the invention, the applicator comprises an elongated strip having finger holes provided at opposite ends for use as handles. The strip spans the back when in use. The strip is comprised of an elastic material of the class known as Neoprene, or Hypalon, etc. This material consists of a thicker layer of closed, expanded bubbles of artificial rubber, and a thinner layer made up of fused pores of the same material bonded, or laminated, to the thicker layer. The layer of closed expanded bubbles is of greater elasticity (stretches more under unit tension) than the layer of fused pores. The thinner layer has a smooth rubber-like surface, and is impermeable. A desired skin product is applied to this non-absorbent surface. The thicker layer of expanded, closed bubbles may be provided with a layer of woven nylon, which does not materially affect either elasticity but may be decorated or colored.

In accordance with the present invention, the applicator 10 comprises an elongated rectangular strip 11 of an impermeable, elastic material characterized by a thicker layer 12 of gas expanded closed bubbles of artificial rubber, bonded or laminated, to a thinner layer 13 of closed pores of, preferably, the same artificial rubber. This thinner layer 13 may be made by heating the top surface of a layer of expanded bubbles until this surface layer melts, discharges the expanding gas, and after cooling, presents a smooth, impermeable, layer 13 of fused material, or pores, integral with the thicker layer 12. This material is known to the trade as "neoprene" and "hypalon", etc., in both its form as single layer of expanded bubbles or the same layer with a thinner layer of closed pores. The side of the strip opposite the thin, impermeable layer may be provided with a laminate decorative strip of woven material such as nylon, which has no substantial effect on elasticity.

Figure 1:
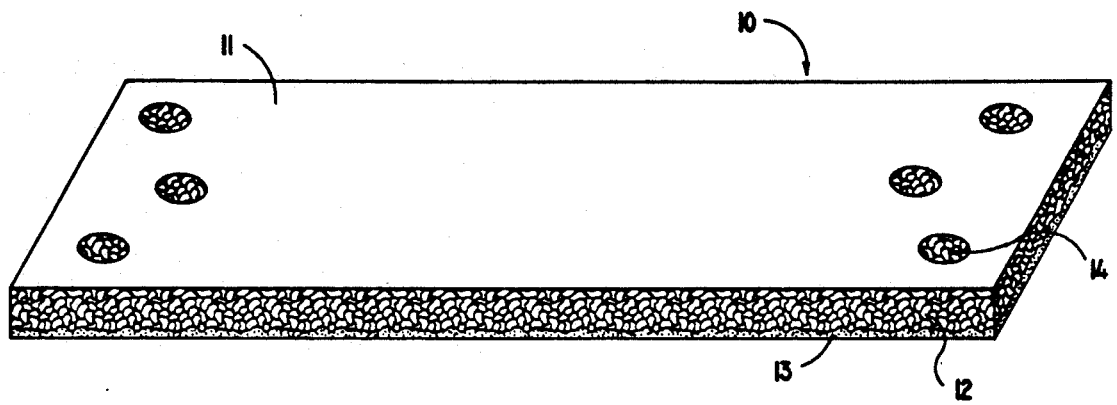
FIG. 1 is an isometric view of a lotion applicator of the invention illustrating the thicker layer of closed expanded bubbles, the thinner layer of closed pores, and the finger holes.
Figure 2:
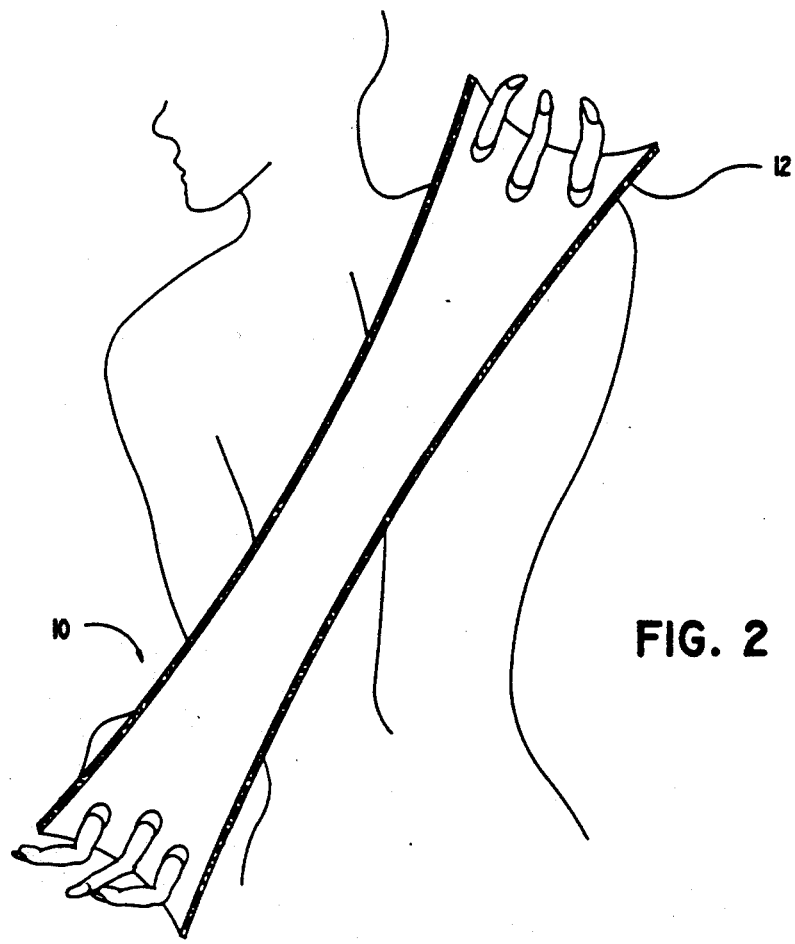
FIG. 2 is a perspective view of the upper portion of a human body viewed from the back, illustrating the applicator supplied to the recess between the shoulder blades.

The thicker layer 12 of expanded bubbles of artificial rubber has less elasticity (requires less unit force to stretch) than the thinner, impermeable,-denser layer 13 of closed pores. Hence, when tension is applied to the strip by fingers in the holes 14, the difference in the respective elasticities of the laminations will cause the thicker layer to cup, and the thinner layer to bulge, as shown in FIG. 2.

It is believed that the phenomenon known as Poisson's Ratio (which is an aspect of elasticity) contributes to this effect. The end portions are held (FIGS. 2 and 3) by the fingers. As shown in FIG. 2, the center of the bulbed portion is below the other portions so that this bulged portion will contact the skin in the recess between the shoulder blades. Lotion previously applied to this bulged portion will therefor be applied to the skin in the recess between the shoulder blades. The woven nylon layer has no effect on this result.

Since the thinner layer 13 is impermeable, no lotion will be lost, and the body will retain it all. The entire applicator may be readily cleaned.

the applicator 10 is provided with at least one, preferably three, holes 14 at each end, spaced about ¾ inch apart, of a diameter to comfortably receive a finger. The strip may be 20 to 40 inches long, and between 2½ inches to 6 inches wide. The strip 12 should be thick enough to give lateral support. A thickness of 5/32 inch is preferred.

In use, the applicator is laid flat with the smooth, impermeable surface up. Lotion is smeared on the center of the applicator. The applicator is grasped by inserting one's fingers into finger holes 14, fingers downward and palms outward. With arms and hands spaced apart, the applicator is swung over and behind the head so that the center of the applicator is opposite the recessed portion of the back between the shoulder blades, and the end portions are generally aligned with the spine. The applicator is then tensioned, so that the center portion will bulge to the shape of FIG. 2, while the end portions may or may not contact the back. The effect is that the bulge is below the end portions so that the bulged portion contacts the recessed skin area between the blades and applies lotion thereto. The applicator may then be pulled from end to end, up and down, or diagonally to apply the lotion over the entire back area. Areas other than the back may receive lotion also.

The bulge of the applicator will yield, or distort, with an application of a very small force. The effect of this on the skin when the applicator is in use is a soft, caressing feeling. The bulge thus conforms itself to the various curves of the body to cover a greater area with a uniform layer of lotion.

The bulging may be enhanced or reduced, as desired, by manipulation of the fingers, while the applicator is in use. Thus the center finger, in the three hole version, may be brought out of alignment with the other two, to enhance the bulging, or the reverse.

From the foregoing, it will be appreciated that the applicator of the invention enables one to easily and evenly spread skin products on inaccessible parts of the body with the non-absorbent surface of the applicator ensuring that little or none of the skin product is wasted. Further, the finger holes of the invention enable one to have greater control in manipulating the applicator, thereby allowing one to achieve greater success in bringing the applicator into contact with hard-to-reach areas of the back. Moreover, the applicator's flexible, elastic nature advantageously still, the present invention can advantageously be provided in a disposable throwaway form that can be packaged with lotion, or the like, included therewith, so that upon removal, the applicator is immediately ready for use. Finally, the present invention is mechanically simple and inexpensively manufactured.

We claim:

1. A method of applying lotion to the human body comprising the steps of
    applying the lotion to a surface of an elongated strip of material having two ends;
    grasping each of said ends with respective hands;
    bulging the lotion receiving side of said strip by tensioning the strip;
    contacting the bulged portion with the lotion thereon to an area of said body.

2. The method of claim 1 wherein the said area of said body is a recessed area.

* * * * *